US006418805B1

(12) United States Patent
Carney et al.

(10) Patent No.: US 6,418,805 B1
(45) Date of Patent: Jul. 16, 2002

(54) CONSTITUENT SENSING SYSTEM

(75) Inventors: Kevin J. Carney, North Andover; John S. Brown, Andover, both of MA (US)

(73) Assignee: Textron Systems Corporation, Wilmington, MA (US)

( * ) Notice: Subject to any disclaimer, the term of this patent is extended or adjusted under 35 U.S.C. 154(b) by 0 days.

(21) Appl. No.: 09/442,576

(22) Filed: Nov. 18, 1999

(51) Int. Cl.$^7$ .................. G01N 33/02; G01N 33/00; G01N 21/85

(52) U.S. Cl. .................. 73/866; 73/866.4; 73/865.3; 73/866.5; 374/142

(58) Field of Search ................ 73/866, 866.5, 73/866.4, 865.3, 1.01, 54.28, 54.35, 861.73, 864.91; 374/142, 208

(56) References Cited

U.S. PATENT DOCUMENTS

| | | | |
|---|---|---|---|
| 3,281,597 A | 10/1966 | Greenberg | 250/43.5 |
| 3,773,424 A | 11/1973 | Selgin | 356/181 |
| 4,003,660 A | 1/1977 | Christie, Jr. et al. | 356/178 |
| 4,260,262 A | 4/1981 | Webster | 356/418 |
| 4,260,263 A | 4/1981 | Kummer | 356/448 |
| 4,266,878 A | 5/1981 | Auer | 356/419 |
| 4,286,327 A | 8/1981 | Rosenthal et al. | 356/416 X |
| 4,403,191 A | 9/1983 | Satake | 324/452 |
| 4,441,979 A * | 4/1984 | Dailey | 204/402 |
| 4,540,286 A | 9/1985 | Satake et al. | 356/445 |
| 4,627,008 A | 12/1986 | Rosenthal | 856/416 X |
| 4,658,147 A | 4/1987 | Eldering | 356/328 |
| 4,692,620 A | 9/1987 | Rosenthal | 250/343 |
| 4,729,247 A * | 3/1988 | Brown | 73/1.34 X |
| 4,752,689 A | 6/1988 | Satake | 250/339 |
| 4,806,764 A | 2/1989 | Satake | 250/339 |
| 4,968,143 A | 11/1990 | Weston | 356/328 |
| 4,997,280 A | 3/1991 | Norris | 356/308 |
| 5,021,662 A | 6/1991 | Johnson | 250/339 |
| 5,092,819 A | 3/1992 | Schroeder et al. | 460/7 |
| 5,106,339 A | 4/1992 | Braun et al. | 460/7 |
| 5,128,882 A | 7/1992 | Cooper et al. | 364/550 |
| 5,148,288 A | 9/1992 | Hannah | 358/298 |
| 5,155,628 A | 10/1992 | Dosmann | 359/640 |
| 5,159,199 A | 10/1992 | LaBaw | 250/339 |
| 5,166,755 A | 11/1992 | Gat | 356/419 |
| 5,179,025 A * | 1/1993 | Koontz et al. | 436/52 |

(List continued on next page.)

FOREIGN PATENT DOCUMENTS

| | | | |
|---|---|---|---|
| DE | 2938-844 | 9/1979 | .......... G01N/21/17 |
| EP | 0 491 131 A1 | 6/1992 | |
| EP | 0 806 653 | 5/1997 | |
| JP | 138043 | 10/1992 | .......... G01N/21/85 |
| WO | WO 96/08710 | 3/1996 | |
| WO | WO 98/11410 | 3/1998 | |
| WO | WO 99/40419 | 8/1999 | |

OTHER PUBLICATIONS

Derwent abstract of SU 514111 A Acc. No.: 1977–A3525Y "Model radial axial hydraulic turbine installation—with test probe holder at lower blade ring" Assignee Lened Metal wks, Jun. 1976.*

Wetzel, D., "Near–Infrared Reflectance Analysis, Sleeper Among Spectroscopic Techniques," *Analytical Chemistry*, 55(12) :1165A–1176A (Oct. 1983).

Goddu, R.F., and Delker, D.A., "Spectra–Structure Correlations for the Near–Infrared Region," Aids for the Analyst. In *Analytical Chemistry*, 32(1) :140–141 (Jan. 1960).

(List continued on next page.)

*Primary Examiner*—Thomas P. Noland
(74) *Attorney, Agent, or Firm*—Foley, Hoag & Eliot LLP

(57) ABSTRACT

The present invention is directed to a constituent sensing system including a container for holding a flowable product. A moveable member is positioned within the container for moving the flowable product within the container in a manner which simulates a flow of the flowable product. A probe is positioned proximate to the moving flowable product for analyzing the moving flowable product.

22 Claims, 3 Drawing Sheets

U.S. PATENT DOCUMENTS

| | | | |
|---|---|---|---|
| 5,205,293 A | * 4/1993 | Ito et al. | |
| 5,206,699 A | 4/1993 | Stewart et al. | 356/30 |
| 5,218,207 A | 6/1993 | Rosenthal | 250/341 |
| 5,241,178 A | 8/1993 | Shields | 250/339 |
| 5,258,825 A | 11/1993 | Reed et al. | 356/402 |
| 5,260,584 A | 11/1993 | Popson et al. | 250/571 |
| 5,272,518 A | 12/1993 | Vincent | 356/405 |
| 5,319,200 A | 6/1994 | Rosenthal et al. | 250/341 |
| 5,327,708 A | 7/1994 | Gerrish | 56/1 |
| 5,351,117 A | 9/1994 | Stewart et al. | 356/30 |
| 5,377,000 A | 12/1994 | Berends | 356/73 |
| 5,383,452 A | 1/1995 | Buchert | 128/633 |
| 5,406,084 A | 4/1995 | Tobler et al. | 250/339.01 |
| 5,433,197 A | 7/1995 | Stark | 128/633 |
| 5,459,313 A | 10/1995 | Schrader et al. | 250/223 |
| 5,460,177 A | 10/1995 | Purdy et al. | 128/633 |
| 5,461,229 A | 10/1995 | Sauter et al. | 250/253 |
| 5,464,981 A | 11/1995 | Squyres et al. | 250/341.8 |
| 5,475,201 A | 12/1995 | Pike | 219/497 |
| 5,476,108 A | 12/1995 | Dominguez et al. | 131/108 |
| 5,480,354 A | 1/1996 | Sadjadi | 460/7 |
| 5,489,980 A | 2/1996 | Anthony | 356/308 |
| 5,502,799 A | 3/1996 | Tsuji et al. | 395/131 |
| 5,503,006 A | * 4/1996 | Babaien-Kibela et al. | 73/86 |
| 5,510,619 A | 4/1996 | Zachmann et al. | 250/339.08 |
| 5,548,115 A | 8/1996 | Ballard et al. | 250/253 |
| 5,616,851 A | 4/1997 | McMahon et al. | 73/29.01 |
| 5,625,459 A | 4/1997 | Driver | 356/446 |
| 5,642,498 A | 6/1997 | Kutner | 395/157 |
| 5,654,496 A | * 8/1997 | Thompson | 73/1.01 |
| 5,676,143 A | 10/1997 | Simonsen et al. | 128/633 |
| 5,684,582 A | 11/1997 | Eastman et al. | 356/328 |
| 5,736,410 A | 4/1998 | Zarling et al. | 356/346 |
| 5,739,536 A | 4/1998 | Bucholtz et al. | 250/341.2 |
| 5,745,234 A | 4/1998 | Snail et al. | 356/236 |
| 5,751,421 A | 5/1998 | Wright et al. | 356/328 |
| 5,784,158 A | 7/1998 | Stanco et al. | 356/326 |
| 5,808,305 A | 9/1998 | Leidecker et al. | 250/341.8 |
| 5,813,987 A | 9/1998 | Modell et al. | 600/473 |
| 5,824,567 A | 10/1998 | Shih et al. | 438/73 |
| 5,847,825 A | 12/1998 | Alexander | 356/318 |
| 5,867,265 A | 2/1999 | Thomas | 356/328 |
| 5,872,655 A | 2/1999 | Seddon et al. | 359/588 |
| 5,880,826 A | 3/1999 | Jung et al. | 356/73 |
| 5,884,775 A | 3/1999 | Campbell | 209/581 |
| 5,953,119 A | 9/1999 | Zigler et al. | 356/326 |
| 5,957,773 A | * 9/1999 | Olmsted et al. | 460/7 |
| 6,100,526 A | * 8/2000 | Mayes | 250/339.11 |

OTHER PUBLICATIONS

Mosen, A.W., and Buzzelli, G., "Determination of Impurities in Helim by Gas Chromatography," Aids for the Analyst. In *Analytical Chemistry*, 21(1) :141–142 (Jan. 1960).

Starr, C., et al., "Applications of Near Infrared Reflectance Analysis in Breeding Wheats for Bread–making Quality," Near Infrared Analysis—Today or Tomorrow? In *Anal. Proc.*, 20:72–74 (Feb. 1983).

Winch, J.E., and Major, H., "Predicting Nitrogen and Digestibility of Forages Using Near Infrared Reflectance Photometry," *Canadian Journal of Plant Science* 61:45–51 (Jan. 1981).

"Discriminant Analysis of Black Tea by Near Infrared Reflectance Spectroscopy," In *Food Chemistry*, G.G. Birch et al., eds. (England: Elsevier Applied Science Publishers Ltd.) 29(1) :233–238 (1988) month not given.

Kisner, H.J, et al., "Multiple Analytical Frequencies and Standards for the Least–Squares Spectrometric Analysis of Serum Lipids," *Analytical Chemistry*, 55(11) :1703–1707 (Sep. 1983).

Ciurczak, E.W., "Uses of Near–Infrared Spectroscopy in Pharmaceutical Analysis," *Applied Spectroscopy Reviews*, 23(1&2) :147–163 (1987) month not given.

Geladi, P., et al., "Linearization and Scatter–Correction for Near–Infrared Reflectance Spectra of Meat," *Applied Spectroscopy*, 39(3) :491–500 (1985) month not given.

Nyden, M.R., et al., "Spectroscopic Quantitative Analysis of Strongly Interacting Systems: Human Plasma protein Mixtures," *Applied Spectroscopy* 42(4) :588–588–594 (1988) month not given.

Watson, C.A., "Near Infrared Reflectance Spectrophotometric Analysis of Agricultural Products," Instrumentation, In *Analytical Chemistry*, 49(9) :835A–840A (Aug. 1977).

Josefson, Mats, et al., "Optical Fiber Spectrometry in Turbid Solutions by Multivariate Calibration Applied to Tablet Dissolution Testing," *Analytical Chemistry*, 60(24) :2666–2671 (Dec. 15, 1988).

Honigs, D.E., et al., "Near–Infrared Reflectance Analysis by Gauss–Jordan Linear Algebra," *Applied Spectroscopy*, 37(6) :Errata, 491–497 (1983) month not given.

Honigs, D.E., et al., "A New Method for Obtaining Individual Component Spectra from Those of Complex Mixtures," *Applied Spectroscopy*, 38(3) :317–322 (1984) month not given.

Stark, E., and Luchter, K., "Near–Infrared Analysis (NIRA): A Technology for Quantitative and Qualitative Analysis," *Applied Spectroscopy Reviews*, 22(4) :335–399 (1986) month not given.

Norris, K.H., et al., "Predicting Forage Quality by Infrared Reflectance Spectroscopy," *Journal of Animal Science*, 43(4) :889–897 (1976) month not given.

Keefe, P.D., "A dedicated wheat grain image analyser," *Plant Varieties and Seeds*, 5:27–33 (1992) month not given.

Suppliers of Kestrel™ brand systems for imaging spectroscopy. Rhea Corporation Home Page, http://home.navisoft-.com/rheacorp/ (Sep. 22, 1997 6:57 AM) 1 page.

Yamamoto, K.Y., et al., "Detection of Metals in the Environment Using a Portable Laser–Induced Breakdown Spectroscopy Instrument," Detection of Metals in the Environment Us . . . Induced Breakdown Spectroscopy Instrument, http://esther.la.asu.edu/sas/journal/ASv50n2/ ASv50n2__sp12.html (Sep. 22, 1997 7:08 AM) 1 page.

Baird, W., and Nogar, N.S., "Compact, Self–Contained Optical Spectrometer," Compact, Self–Contained Optical Spectrometer, http://esther.la.asu.edu/sas/journal/ASv49n11/ Asv49n11–sp20.html (Sep. 22, 1997 7:12 AM) 1 page.

"Perstorp Analytical," Perstorp Analytical Products, http://www.i–way.net.uk/sinar/products/ (Sep. 22, 1997 7:31 AM) 1 page.

"Grain Flow and Moisture Sensor Calibration," Department of Biosystems and Agricultural Engineering, 1995 Annual Report http://www.bae/umn/edu/annrpt/1995/research/machl.html (Sep. 22, 1997 7:33 AM).

Lutton, C., "Cyberfarm," Computers/Communications, In *Forbes*, pp. 86–87 (Jul. 15, 1996).

"Infrared detectors," Near Infrared Spectroscopy in Food Analysis, In *Fundamentals of Near Infrared Instrumentation*, pp. 71–73 (undated) but by Feb. 2000.

"Better Crops with Plant Food," 81(4) (1997) month not given 24 pages.

Schneider, I., et al., "Fiber–Optic Near–Infared Reflectance Sensor for Detection of Organics in Soils," *IEEE Photonics Technology Letters*, 7(1) :87–89 (Jan. 1995) from 250/339–11.

* cited by examiner

CONSTITUENT SENSING SYSTEM

BACKGROUND

It has been long recognized that the value of agricultural products such as cereal grains and the like are affected by the quality of their inherent constituent components. Examples of such agricultural products are wheat, corn, rye, oats, barley, rice, soybeans, amaranth, triticale, grasses and forage materials. Cereal grains with desirable protein, oil, starch, fiber and moisture content and desirable levels of carbohydrates and other constituents can command a premium price. Favorable markets for these grains and their processed commodities have, therefore, created the need for knowing content and also various other physical characteristics such as hardness.

To meet market expectations, numerous analysis systems have been developed. Some of these analysis systems are installed within equipment such as a combine harvester, grain elevator or other grain processing equipment for determining percentage concentration of constituents in a flowing stream of grain while the grain is harvested, stored or processed.

SUMMARY OF THE INVENTION

The present invention provides a grain sample sensing system which can be used by itself for analyzing constituent components of grain or in conjunction with analysis systems incorporated within combine harvesters, grain elevators, or other grain processing equipment. When used in conjunction with such equipment, the grain sample sensing system can be used to calibrate analysis systems already contained within or for later installation in the equipment. The grain sample sensing system can also be used to merely verify the accuracy of the analysis systems. The present invention system includes a container for holding grain. A moveable member is positioned within the container for moving the grain within the container in a manner which simulates a flow of grain. A probe is positioned proximate to the moving grain for analyzing the moving grain.

In preferred embodiments, the container is stationary and has a round side wall. The moveable member rotates within the container to move the grain in a circular manner inside the container. The moveable member is driven by a variable speed motor which allows the rotational speed of the moveable member to be varied. The probe analyzes the moving grain in real time where different constituent components of the moving grain are measured at the same moment of time from the same fraction of grain. A thermocouple is also positioned within the container for sensing grain temperature. The container is covered by a lid which includes a grain loading door for loading the container with grain. The container also includes a grain discharge door on a lower surface of the container to allow grain to be removed from the container.

The present invention grain sample sensing system is suitable for calibrating analysis systems already contained within or for later installation in grain processing equipment because the rotation of the grain within the container simulates the flow of grain in a chute or conduit of such equipment. As a result, the present invention system makes analysis readings under approximately the same conditions of such equipment.

The present invention also provides a constituent sensing system for analyzing constituent components of a flowable product. The constituent sensing system includes a container for holding the flowable product. A moveable member is positioned within the container for moving the flowable product within the container in a manner which simulates a flow of the flowable product. A probe is positioned proximate to the moving flowable product for analyzing the moving flowable product.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
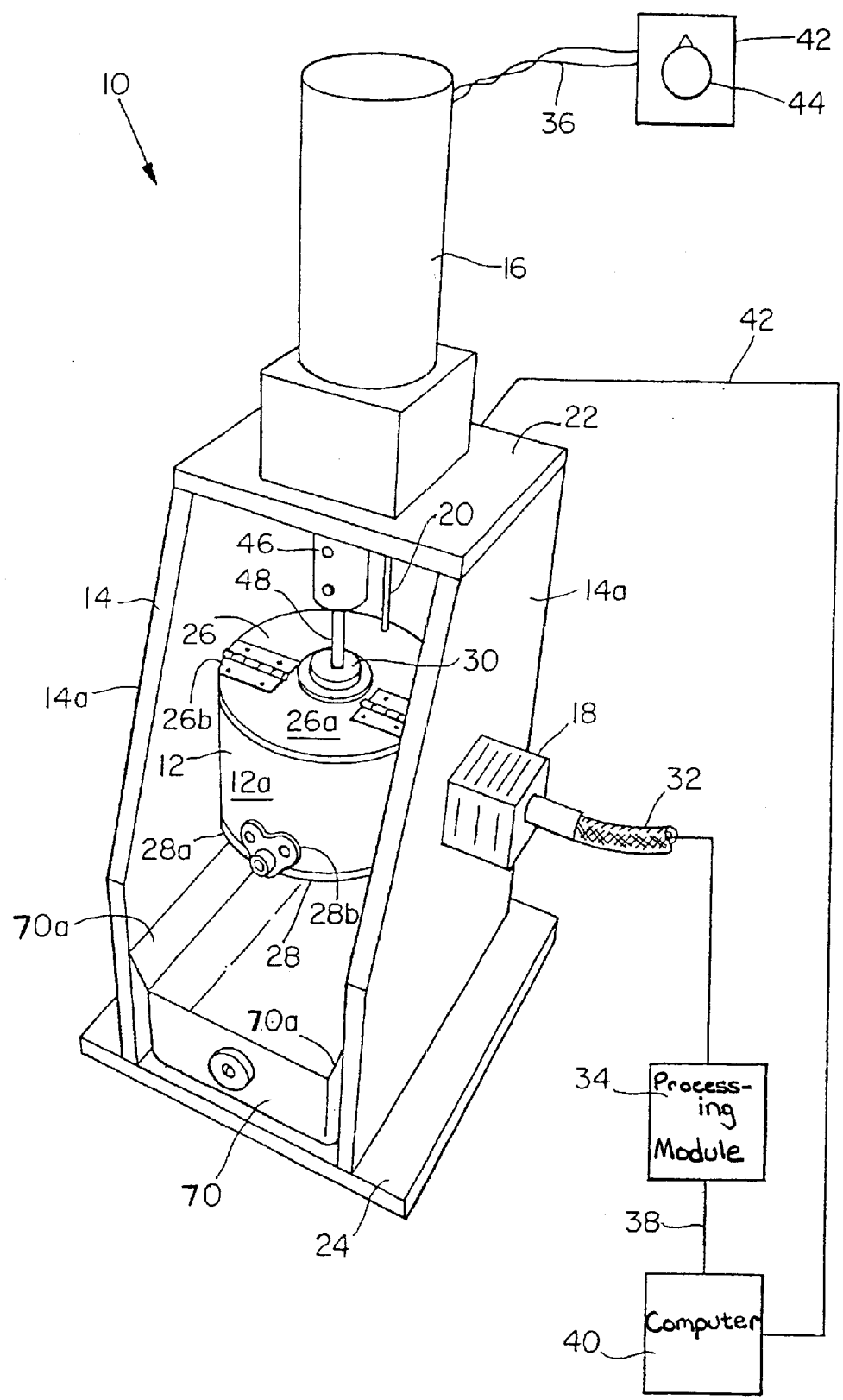
FIG. 1 is a perspective view of the present invention grain sample sensing system.
Figure 2:
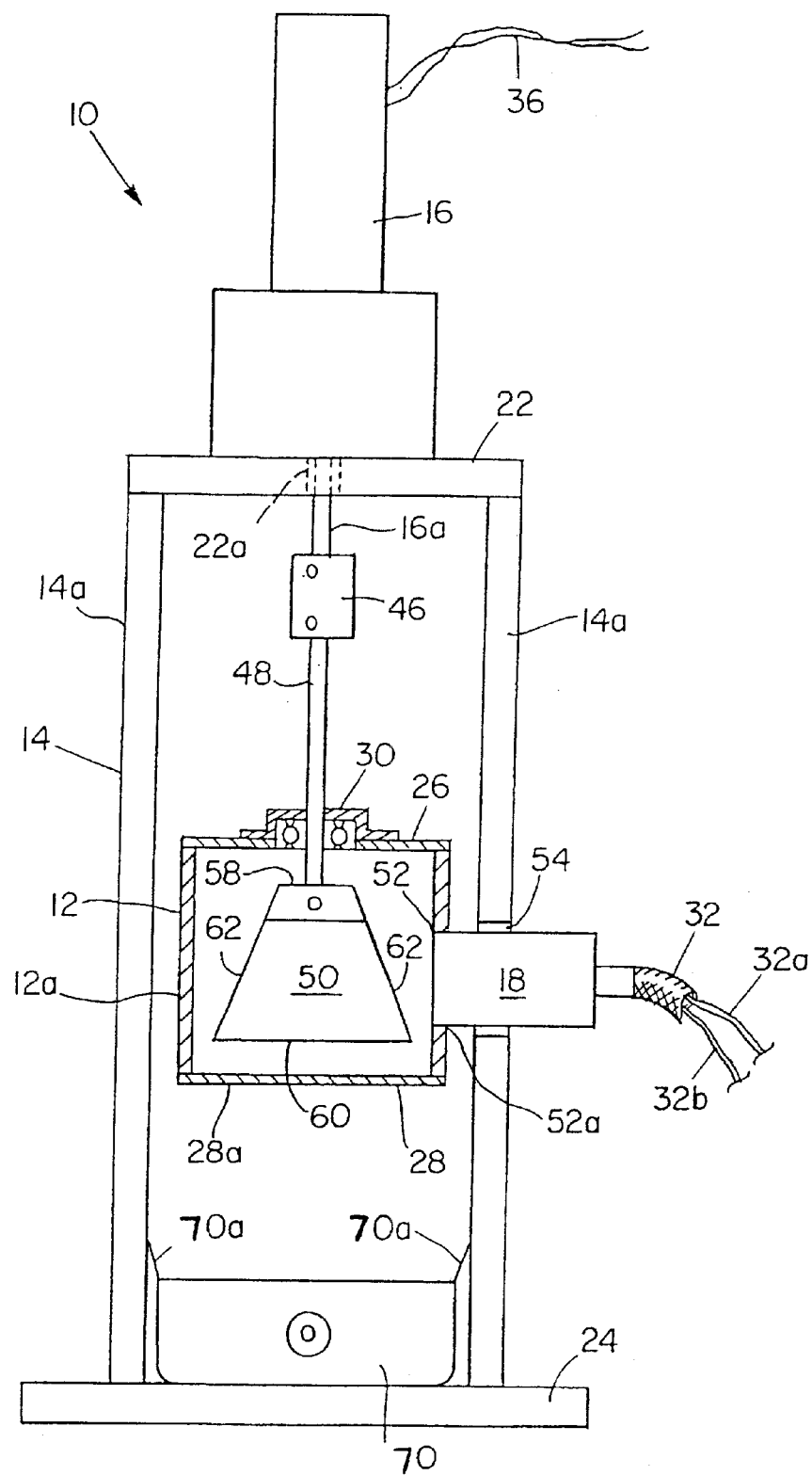
FIG. 2 is a front view of the present invention grain sample sensing system with the grain bowl in section to show the interior.
Figure 3:
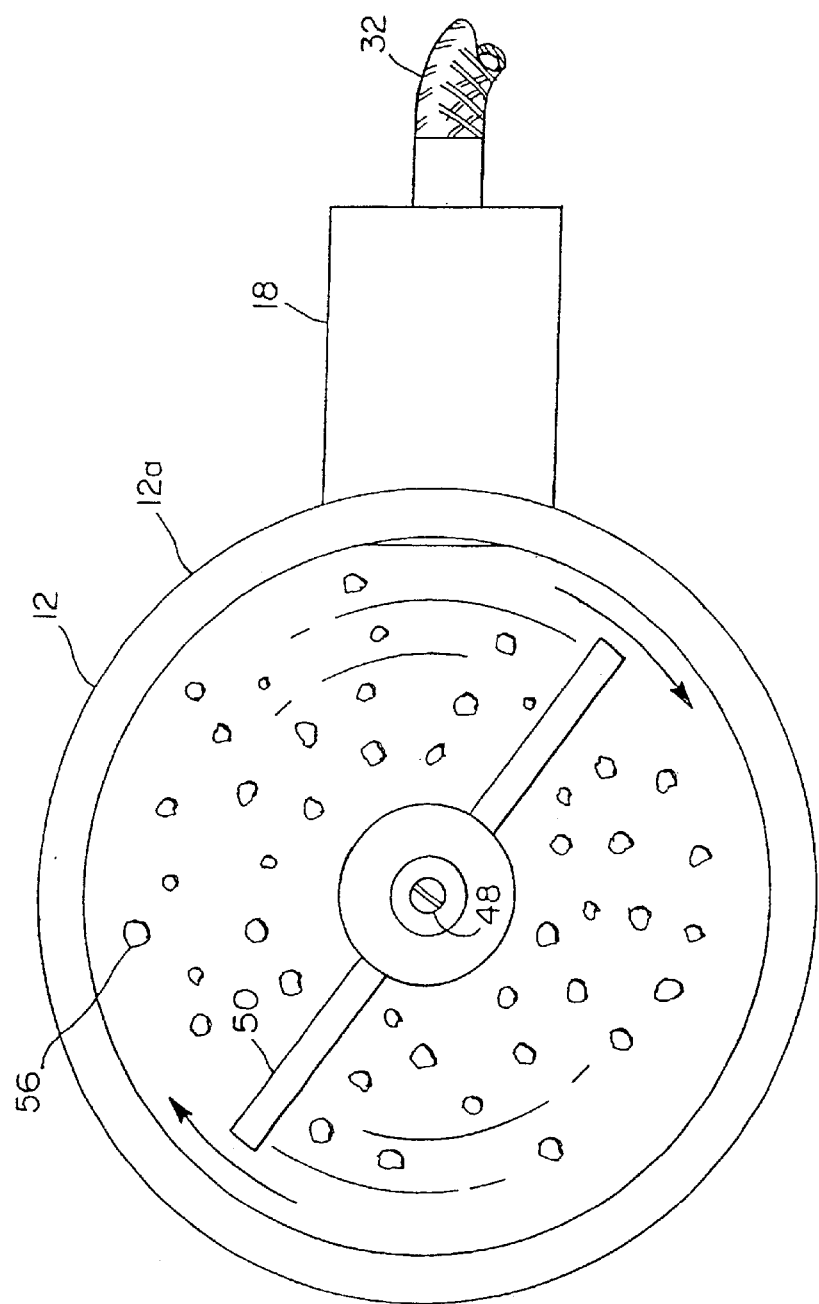
FIG. 3 is a top view of the grain bowl with the top removed.

Referring to FIGS. 1, 2 and 3, grain sample sensing system 10 is capable of analyzing constituent components or elements of agricultural products such as grain, for example, protein, oil, starch, fiber, moisture and carbohydrate content as well as physical characteristics such as hardness. Grain sample sensing system 10 includes a grain bowl 12 with a circular side wall 12a for holding a sample of grain 56 (FIG. 3) to be analyzed. Grain bowl 12 has a grain loading door 26a on the top 26 of grain bowl 12 for loading grain 56 into grain bowl 12 for analysis and a grain discharge door 28a on the bottom 28 of grain bowl 12 for removing grain 56 from grain bowl 12 after analysis. Grain bowl 12 is supported by a support frame 14. Support frame 14 has a bottom plate 24, two opposed side walls 14a extending upwardly from bottom plate 24, and a top plate 22 extending between side walls 14a. Grain bowl 12 is supported between the side walls 14a of support frame 14 above bottom plate 24. A variable speed drive motor 16 is mounted above grain bowl 12 to the upper surface of top plate 22. A power supply 42 provides power to drive motor 16 via power lines 36. Power supply 42 has a variable speed dial 44 for controlling the speed of drive motor 16. Drive motor 16 has a rotatable drive shaft 16a for rotating a moveable member or paddle 50 within grain bowl 12 (FIGS. 2 and 3). Drive shaft 16a extends downwardly from drive motor 16 and is coupled by a coupling 46 to a paddle shaft 48 extending upwardly from paddle 50. Rotation of the paddle 50 within grain bowl 12 moves the grain 56 in a circular direction within grain bowl 12 to simulate flowing grain.

An analysis probe 18 extends through a side wall 14a of support frame 14 and through side wall 12a of grain bowl 12 for analyzing different constituent components of rotating grain 56 as the grain 56 (FIG. 3) moves past probe 18. Probe 18 contains a light source for irradiating the grain 56 simultaneously with multiple radiation wavelengths and a light pickup for receiving radiation diffusely reflected from a discrete portion of the grain 56. A processing module 34 is connected to probe 18 by a line 32 for receiving the reflected light from the light pickup (FIG. 1). Line 32 contains a fiber optic cable 32a for transmitting the reflected light as well as power and signal lines 32b for the light source (FIG. 2). Processing module 34 processes the light and converts the light with spectroscopy techniques into data regarding different constituent components of grain 56. A computer 40 electrically connected to processing module 34 by line 38 allows the constituent component data to be viewed.

The thermocouple 20 for sensing the temperature of grain 56 within grain bowl 12 extends through the top 26 of grain bowl 12 (FIG. 1). Thermocouple 20 is electrically connected to computer 40 by line 42. A grain discharge drawer 70 is slidably positioned on the bottom plate 24 of frame 14 between side walls 14a and under grain bowl 12 for catching grain 56 discharged from grain bowl 12 after analysis through discharge door 28a. Grain discharge drawer 70 includes angled upper surfaces 70a for deflecting falling grain 56 into grain discharge drawer 70.

A more detailed description of grain sample sensing system 10 now follows. Top plate 22 has an opening 22a therethrough which allows drive shaft 16a of drive motor 16 to extend through top plate 22 (FIG. 2). A bearing 30 assembly mounted to the top 26 of grain bowl 12 supports paddle shaft 48 as paddle shaft 48 extends through a hole in the top 26 of grain bowl 12. Paddle 50 is flat in shape with a trapezoidal outer perimeter. Paddle 50 is positioned within grain bowl 12 such that the top 58, bottom 60 and side 62 edges of paddle 50 are spaced apart from the inner surfaces of the top 26, bottom 28 and side wall 12a of grain bowl 12 to form gaps therebetween. Side edges 62 of paddle 50 angle away from side wall 12a, thereby reducing the possibility of interfering with the operation of probe 18 by reflecting light. Grain loading door 26a is pivotably secured to the top 26 of grain bowl 12 by two hinges 26b (FIG. 1). The grain discharge door 28a of grain bowl 12 is pivotably secured to the bottom 28 of grain bowl 12 by two hinges 28b.

Probe 18 is mounted to a probe mount 52a on grain bowl 12 and extends into side wall 12a of grain bowl 12 through a probe opening or window 52 to be about 0.1 inches away from the grain 56 when the grain 56 moves past the probe 18 during use (FIGS. 2 and 3). Probe 18 is preferably a near infrared analysis probe which includes a broad bandwidth light source for irradiating the grain 56 simultaneously with multiple radiation wavelengths from about 570 to 1120 nm. The light source of probe 18 generates light having all the wavelengths necessary for detecting the desired constituent components of grain 56.

Probe 18 includes a fiber optic light pickup for receiving radiation reflected from the moving grain 56. The fiber optic cable 32a within line 32 transmits the received light to processing module 34 which processes the light with spectroscopy techniques to determine the desired constituent components of the grain 56 based on the processed light (FIG. 1). The processing module 34 is electrically connected to computer 40 so that the data regarding the constituent components of grain 56 can be viewed on the screen of computer 40 or printed out. Alternatively, the data can be sent to a display screen of a combine harvester. Probe 18 and processing module 34, along with the associated hardware and software, are similar to that disclosed in U. S. patent application Ser. No. 09/019,667, filed Feb. 6, 1998, now U.S. Pat. No. 6,100,526, entitled "Grain Quality Monitor", the entire teachings of which are incorporated herein by reference.

Grain sample sensing system 10 measures all the desired constituent components of grain 56 from the reflected light at the same moment in time (real time) from the same fraction of the grain sample 56 within grain bowl 12. This differs from analysis systems which measure different constituent components at different points in time so that when measuring flowing grain, each constituent component is measured from a different fraction or segment of the grain sample.

In one preferred embodiment, drive motor 16 is a variable speed 24 amp DC motor capable of generating 55 inch pounds of torque. Drive motor 16 rotates paddle 50 in a clockwise direction, thereby causing the grain 56 to flow in a clockwise direction. The speed of drive motor 16 can be adjusted to move the grain 56 within grain bowl 12 at speeds between about 1 inch/sec to 80 inches/sec. Grain bowl 12 has an outer diameter of about 4.5 inches, an inner diameter of about 4 inches and a height of about 2.75 inches.

In operation, referring to FIG. 1, in order to analyze a sample of grain, the grain loading door 26a of grain bowl 12 is opened and grain bowl 12 is filled preferably about ⅔ full with grain 56. After grain loading door 26a is closed, drive motor 16 is then turned on to rotate paddle 50 within grain bowl 12 (FIG. 3). The speed of drive motor 16 is controlled by the variable speed dial 44 of power supply 42 to rotate or spin the grain 56 within grain bowl 12 at a desired speed. Often, grain sample sensing system 10 is employed to either calibrate or verify the accuracy of an analysis system contained within another piece of equipment, for example, a combine harvester, a grain elevator or other grain processing equipment. In such situations, the same sample of grain is preferably analyzed by both grain sample sensing system 10 and the desired piece of associated grain processing equipment. The speed of drive motor 16 is adjusted until the speed of the grain 56 rotating within grain bowl 12 matches the speed of the grain flowing in the associated grain processing equipment past the analysis probe contained therein. The movement of the grain 56 within the grain bowl 12 past the side wall 12a simulates grain flowing in a chute or conduit of the associated grain processing equipment so that analysis of the grain 56 by grain sample sensing system 10 is performed under approximately the same conditions as within the associated grain processing equipment. This ensures that the readings are accurate. Once the grain 56 is rotating at the proper speed, analysis readings for the desired constituent components are made by grain sample sensing system 10, for example, protein, oil, starch, fiber, moisture and carbohydrate content as well as hardness. The readings of the measured constituent components of the grain 56 are made simultaneously at a particular instant in time so that the readings are from a particular fraction of the grain 56 sample. In addition, the temperature of grain 56 is sensed by thermocouple 20. The readings are displayed on the screen of computer 40. The analysis system in the associated grain processing equipment can then be adjusted so that the readings match those of grain sample sensing system 10 if calibration is desired. If the readings match, the accuracy of the associated analysis system is verified and no calibration is necessary. If grain sample sensing system 10 is employed for calibrating probes 18 which are later installed within a piece of grain processing equipment, probe 18 in grain sample sensing system 10 is adjusted until the readings match those of an analysis system contained within another previously calibrated grain sample sensing system 10 or grain processing equipment.

Multiple readings made by grain sample sensing system 10 for a particular grain 56 sample can be used to form an average of the whole sample of grain 56. A reading that is abnormal relative to the other readings is readily identifiable and can be discarded. In prior art analysis systems where the readings for the measured constituent components are taken over a period of time as a large amount of grain passes by the analysis probe, the readings can be inaccurate if any constituent component measurements are taken from a small abnormal portion of grain flowing past the analysis probe. Although grain sample sensing system 10 is often employed in conjunction with a piece of associated grain processing equipment, alternatively, grain sample sensing system 10 can be employed as a stand alone system for monitoring samples in the field or in the lab.

While this invention has been particularly shown and described with references to preferred embodiments thereof, it will be understood by those skilled in the art that various changes in form and details may be made therein without departing from the spirit and scope of the invention as defined by the appended claims.

For example, the size of grain bowl 12 can be varied to suit different requirements. The size of drive motor 16 would be varied depending upon the size of grain bowl 12. Although thermocouple 20 and probe 18 are depicted as entering within grain bowl 12 through the top 26 and side wall 12a respectively, the thermocouple 20 and probe 18 can be inserted into grain bowl 12 at any suitable location or orientation. Thermocouple 20 can also be omitted. In addition, paddle shaft 48 can extend into grain bowl 12 from the bottom 28 or through side wall 12a along a horizontal axis. Extending paddle shaft 48 through side wall 12a would rotate paddle 50 along the horizontal axis, thereby rotating grain 56 in an upright manner. In such cases, grain bowl 12 would be shaped appropriately and the drive motor 16 would be mounted in a suitable fashion. Drive motor 16 can be mounted directly to grain bowl 12 with support frame 14 being omitted. Also, drive motor 16 can be replaced by a handcrank coupled to paddle shaft 48 for rotating paddle 50 by hand. Furthermore, although probe 18 has been described for use in grain sample sensing system 10, other suitable analysis probes can be employed. Grain sample sensing system 10 can be employed as a constituent sensing system for analyzing particulate materials other than the previously mentioned agricultural products, such as crushed minerals, crushed ore, ash, soil, manure, etc. Also, other flowable compositions, mixtures or products such as blood or paint can be analyzed with system 10. It is understood that system 10 can be used either in conjunction with associated processing equipment or as a stand alone unit when sensing non agricultural products.

What is claimed is:

1. A grain sample sensing system comprising:
   a container for holding grain;
   a moveable member positioned within the container for moving the grain within the container in a manner which simulates a flow of grain; and
   a probe positioned proximate to the moving grain for analyzing the moving grain.

2. The system of claim 1 in which the moveable member rotates within the container to move the grain in a circular path.

3. The system of claim 2 in which the container is stationary.

4. The system of claim 3 in which the moveable member is driven by a motor.

5. The system of claim 4 in which the motor is a variable speed motor capable of varying the rotational speed of the moveable member.

6. The system of claim 1 in which the probe analyzes the moving grain in real time.

7. The system of claim 1 in which the probe measures different constituent components of the moving grain at the same time.

8. The system of claim 1 further comprising a thermocouple within the container for sensing grain temperature.

9. The system of claim 1 further comprising a lid covering the container, the lid having a grain loading door for loading the container with grain.

10. The system of claim 9 further comprising a grain discharge door on a lower surface of the container for removing grain from the container.

11. A grain sample sensing system comprising:
    a container for holding grain;
    a moveable member rotating within the container for moving the grain with the container in a circular path which simulates a flow of grain;
    and a probe positioned proximate to the moving grain for analyzing the moving grain in real time.

12. The system of claim 11 in which the moveable member is driven by a motor.

13. The system of claim 12 in which the motor is a variable speed motor for varying the rotational speed of the moveable member.

14. The system of claim 11 in which the probe measures different constitutent components of the moving grain at the same time.

15. An agricultural product sample sensing system comprising:
    a container for holding an agricultural product;
    a moveable member positioned within the container for moving the agricultural product within the container in a manner which simulates a flow of agricultural product; and
    a probe positioned proximate to the moving agricultural product for analyzing the moving agricultural product.

16. A method of analyzing grain comprising the steps of:
    holding the grain with a container;
    moving the grain within the container in a manner which simulates a flow of grain with a moveable member positioned within the container; and
    analyzing the moving grain with a probe positioned proximate to the moving grain.

17. The method of claim 16 in which the step of moving the grain comprises rotating the moveable member within the container to move the grain in a circular path.

18. The method of claim 17 further comprising the step of driving the moveable member with a motor.

19. The method of claim 16 in which the step of analyzing the grain comprises analyzing the moving grain in real time.

20. The method of claim 16 in which the step of analyzing the moving grain comprises measuring different constituent components of the moving grain at the same time.

21. The method of claim 16 further comprising the step of sensing grain temperature with a thermocouple positioned within the container.

22. A method of analyzing an agricultural product comprising the steps of:
    holding the agricultural product within a container;
    moving the agricultural product within the container in a manner which simulates a flow of agricultural product with a moveable member positioned within the container; and
    analyzing the moving agricultural product with a probe positioned proximate to the moving agricultural product.

* * * * *